US009504748B2

(12) United States Patent
Cauvin et al.

(10) Patent No.: US 9,504,748 B2
(45) Date of Patent: Nov. 29, 2016

(54) AQUEOUS SILICONE DISPERSIONS AND THEIR PREPARATION

(71) Applicant: Dow Corning Corporation, Midland, MI (US)

(72) Inventors: Severine Cauvin, Mons (BE); Morgane Le Meur, Brussels (BE); Jonathan Thill, Pont-A-Celles (BE); Xavier Jean-Paul Thomas, Famars (FR)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/413,329

(22) PCT Filed: Jul. 15, 2013

(86) PCT No.: PCT/EP2013/064897
§ 371 (c)(1),
(2) Date: Jan. 7, 2015

(87) PCT Pub. No.: WO2014/019840
PCT Pub. Date: Feb. 6, 2014

(65) Prior Publication Data
US 2015/0157724 A1 Jun. 11, 2015

(30) Foreign Application Priority Data

Aug. 1, 2012 (EP) ..................... 12305951

(51) Int. Cl.
| | |
|---|---|
| A61K 47/34 | (2006.01) |
| A61K 8/39 | (2006.01) |
| A61K 8/73 | (2006.01) |
| A61Q 19/00 | (2006.01) |
| A61K 8/81 | (2006.01) |
| A61K 8/85 | (2006.01) |
| A61K 8/86 | (2006.01) |
| A61K 8/895 | (2006.01) |
| A61K 8/06 | (2006.01) |
| A61L 15/26 | (2006.01) |
| A61L 15/58 | (2006.01) |
| A61F 13/02 | (2006.01) |
| A61K 8/04 | (2006.01) |
| A61K 9/10 | (2006.01) |
| A61K 47/32 | (2006.01) |
| A61F 13/00 | (2006.01) |

(52) U.S. Cl.
CPC ........... *A61K 47/34* (2013.01); *A61F 13/0253* (2013.01); *A61K 8/04* (2013.01); *A61K 8/062* (2013.01); *A61K 8/39* (2013.01); *A61K 8/731* (2013.01); *A61K 8/8129* (2013.01); *A61K 8/85* (2013.01); *A61K 8/86* (2013.01); *A61K 8/895* (2013.01); *A61K 9/10* (2013.01); *A61K 47/32* (2013.01); *A61L 15/26* (2013.01); *A61L 15/58* (2013.01); *A61Q 19/00* (2013.01); *A61F* *2013/0037* (2013.01); *A61F 2013/0071* (2013.01); *A61F 2013/00387* (2013.01); *A61F 2013/00646* (2013.01); *A61F 2013/00702* (2013.01); *A61F 2013/00719* (2013.01); *A61K 2800/594* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 3,159,601 | A | 12/1964 | Ashby |
| 3,220,972 | A | 11/1965 | Lamoreaux |
| 3,296,291 | A | 1/1967 | Chalk et al. |
| 3,419,593 | A | 12/1968 | Willing |
| 3,516,946 | A | 6/1970 | Modic |
| 3,814,730 | A | 6/1974 | Karstedt |
| 3,989,668 | A | 11/1976 | Lee et al. |
| 4,766,176 | A | 8/1988 | Lee et al. |
| 4,784,879 | A | 11/1988 | Lee et al. |
| 4,838,253 | A | 6/1989 | Brassington et al. |
| 4,991,574 | A | 2/1991 | Pocknell |
| 5,017,654 | A | 5/1991 | Togashi et al. |
| 5,036,117 | A | 7/1991 | Chung et al. |
| 5,095,067 | A | 3/1992 | Hara et al. |
| 5,175,325 | A | 12/1992 | Brown et al. |
| 5,399,402 | A | 3/1995 | Inoue et al. |
| 5,500,148 | A | 3/1996 | Ohba et al. |
| 6,238,656 | B1 * | 5/2001 | Morita ..................... A61K 8/89 424/70.12 |

(Continued)

FOREIGN PATENT DOCUMENTS

| | | |
|---|---|---|
| EP | 0484001 | 10/1991 |
| EP | 0347895 | 11/1993 |

(Continued)

OTHER PUBLICATIONS

STN registry entry for Sannonic SS 50 and Sannonic SS 70 (no date).*

(Continued)

*Primary Examiner* — Marc Zimmer
(74) *Attorney, Agent, or Firm* — Warner Norcross & Judd LLP

(57) ABSTRACT

An aqueous dispersion comprises a silicone composition dispersed in an aqueous phase. The silicone composition comprises a product of a reaction of (a) an alkenyl-containing organopolysiloxane having an average per molecule of at least 2 alkenyl groups and (b) an Si H containing siloxane having an average per molecule of at least 2 Si H moieties. The dispersion also comprises a hydrosilylation catalyst, a polymeric film former and a surfactant of molecular weight below 1600. The composition is stabilised in dispersion form by the surfactant dissolved in the aqueous phase and the polymeric film former, and is capable of forming a tacky layer on drying.

19 Claims, No Drawings

(56) References Cited

U.S. PATENT DOCUMENTS

| | | |
|---|---|---|
| 6,306,411 B1 | 10/2001 | Jager Lezer |
| 6,403,704 B1 | 6/2002 | Bara |
| 6,794,444 B2 | 9/2004 | Yamamoto et al. |
| 8,263,666 B2 * | 9/2012 | Noel .................. A61K 8/06 424/401 |
| 8,658,254 B2 | 2/2014 | Delis et al. |
| 9,181,434 B2 | 11/2015 | Shikano et al. |
| 2002/0028223 A1 | 3/2002 | Vatter et al. |
| 2003/0143408 A1 | 7/2003 | Benayoun et al. |
| 2004/0171699 A1 * | 9/2004 | Morita .................. C08J 3/03 516/9 |
| 2005/0089697 A1 | 4/2005 | Benayoun et al. |
| 2005/0119406 A1 | 6/2005 | Duffy et al. |
| 2006/0099346 A1 | 5/2006 | Martin et al. |
| 2006/0122323 A1 | 6/2006 | Dumont et al. |
| 2006/0140896 A1 | 6/2006 | Decoster et al. |
| 2007/0099007 A1 | 5/2007 | Benayoun et al. |
| 2008/0021125 A1 * | 1/2008 | Shirasaki .................. C08J 9/28 521/64 |
| 2010/0196454 A1 | 8/2010 | Keller |
| 2010/0305258 A1 * | 12/2010 | Irifune .................. C08J 3/03 524/503 |
| 2011/0009553 A1 | 1/2011 | Heller et al. |
| 2012/0156148 A1 | 6/2012 | Shikano et al. |
| 2012/0251598 A1 * | 10/2012 | Ikeda .................. C08L 83/04 424/401 |
| 2015/0150975 A1 * | 6/2015 | Tanaka .................. A61K 47/12 424/185.1 |

FOREIGN PATENT DOCUMENTS

| | | |
|---|---|---|
| EP | 587462 | 3/1994 |
| EP | 1070734 | 3/2003 |
| EP | 1447423 | 4/2006 |
| JP | 2005325088 | 11/2005 |
| WO | 2005070384 | 8/2005 |

OTHER PUBLICATIONS

Sigma-Aldrich listing of commercially available nonionic surfactants by HLB value (no date).*

First Office Action of Related Chinese Application No. 201380030712.1, Oct. 23, 2015.

First Office Action of Counterpart Chinese Application No. 201380037534.5, Feb. 4, 2016.

* cited by examiner

AQUEOUS SILICONE DISPERSIONS AND THEIR PREPARATION

This application is a national stage entry of International Patent Application No. PCT/EP2013/064897, filed Jul. 15, 2013, which claims priority to European Patent Application No. EP12305951.1, filed Aug. 1, 2012, the contents of each of which are incorporated herein by reference in their entirety.

This invention relates to aqueous silicone dispersions capable of forming a tacky layer on drying and to a process for the preparation of such dispersions. The invention also relates to a method of coating a substrate with a tacky layer comprising coating the substrate with the aqueous silicone dispersion, and to a method of treating a mammal by topically applying a composition comprising the aqueous silicone dispersion.

U.S. Pat. No. 6,306,411 describes a composition to be applied to the skin and superficial body growths, comprising an aqueous dispersion of particles of film-forming polymer, characterized in that it further comprises an aqueous suspension of particles of at least partially crosslinked solid elastomeric polyorganosiloxane. The elastomeric polyorganosiloxane is obtained by addition reaction and crosslinking in the presence of a catalyst of the platinum type, of at least one polyorganosiloxane containing at least two vinyl groups in position alpha, omega of the silicone chain per molecule, and an organosiloxane containing at least one hydrogen atom linked to a silicon atom per molecule.

U.S. Pat. No. 6,403,704 describes a process for increasing the water-resistance of a cosmetic composition by introducing into the composition particles of an at least partially crosslinked elastomeric polyorganosiloxane suspended in an aqueous phase.

EP-B-1044237 describes an aqueous silicone emulsion useful for preparing anti-adherent coating on paper. Said emulsion comprises polyorganosiloxanes with Si-vinyl units and polyorganosiloxanes with SiH units, cross-linkable by polyaddition in the presence of a platinum catalyst. The emulsion contains a buffer solution for setting and maintaining pH between 5 and 9, an emulsifying agent such as polyvinyl alcohol, and optionally a polyaddition inhibitor. EP-B-587462 and U.S. Pat. No. 5,095,067 describe emulsifying a polyorganosiloxane with Si-vinyl units and a polyorganosiloxane with SiH units together and crosslinking in the presence of a platinum catalyst.

EP1263843 describes the use of a stabilizing hydrophilic (co)polymer for reducing the residual deposits, on the rolls of a coating machine, of silicone derived from silicone emulsions likely to crosslink to form non-stick coatings on flexible supports. The use of this hydrophilic (co)polymer is described to improve the stability of the emulsion before coating and to prevent coalescence.

In a process according to the present invention for the preparation of an aqueous silicone dispersion, the process comprises mixing (a) an alkenyl-containing organopolysiloxane having an average per molecule of at least 2 alkenyl groups and (b) an SiH containing siloxane having an average per molecule of at least 2 SiH moieties, and emulsifying the resulting mixture in an aqueous solution of a polymeric film former and a surfactant of molecular weight below 1600, to form an aqueous silicone emulsion, wherein a hydrosilylation catalyst is added simultaneously with the aqueous polymeric film former and surfactant or is added to the aqueous silicone emulsion subsequently, the alkenyl-containing organopolysiloxane (a) and the SiH containing siloxane (b) being reacted together in the aqueous silicone emulsion, and the alkenyl-containing organopolysiloxane (a) and the SiH containing siloxane (b) and their reaction product being stabilised in dispersion form by the surfactant dissolved in the aqueous phase and the polymeric film former.

By a 'dispersion' we mean a colloidal material having a disperse or discontinuous phase, which may be liquid or solid, dispersed or statistically distributed in a liquid continuous phase. The aqueous silicone dispersion of the invention has a disperse phase of a silicone material, which may be liquid or solid, dispersed in an aqueous liquid continuous phase. An emulsion is a colloidal material having a liquid disperse phase dispersed or statistically distributed in a liquid continuous phase. The alkenyl-containing organopolysiloxane (a) and the SiH containing siloxane (b) are liquids when mixed and when emulsified, but may react within the liquid disperse phase of the emulsion in the presence of the hydrosilylation catalyst to form a solid silicone material. The aqueous dispersion of the invention is capable of forming a tacky layer on drying.

By a surfactant we mean a surface active agent which lower the surface tension of water. The surfactant generally contains both hydrophobic groups and hydrophilic groups. The surfactant has a molecular weight below 1600. The surfactant generally has a solubility in water at 25° C. of at least 10% by weight or is dispersible in water. The polymeric film former is soluble or dispersible in a 10% by weight solution of the surfactant and is capable of forming a coherent film when a 10% by weight solution or dispersion of the polymeric film former in an aqueous solution of the surfactant (in the absence of any silicone material) is deposited on a substrate and dried.

An aqueous dispersion according to the invention, capable of forming a tacky layer on drying, comprises a silicone composition dispersed in an aqueous phase, the silicone composition comprising a product of a reaction of (a) an alkenyl-containing organopolysiloxane having an average per molecule of at least 2 alkenyl groups and (b) an SiH containing siloxane having an average per molecule of at least 2 SiH moieties, the dispersion also comprising a hydrosilylation catalyst, a polymeric film former and a surfactant of molecular weight below 1600, the silicone composition being stabilised in dispersion form by the surfactant dissolved in the aqueous phase and the polymeric film former.

When the aqueous dispersion of the invention is deposited as a film or coated on a substrate and allowed to dry, the disperse phase comprising distinct droplets of reacted silicone composition adheres together as a soft silicone elastomer layer in contact with the substrate. The soft silicone elastomer layer contains the polymeric film former and the surfactant of molecular weight below 1600 and is tacky and useful as an adhesive.

A method according to one aspect of the invention of adhering a dressing to a mammal in need of such treatment comprises coating a surface of a dressing with an effective amount of the aqueous dispersion of the invention, allowing a sufficient amount of water in the aqueous phase to evaporate from the coating on the substrate so as to form a tacky layer on the dressing and applying the tacky layer on the dressing to a portion of skin of the mammal. An alternative method according to the invention of adhering a dressing to a mammal in need of such treatment comprises topically applying an effective amount of the dispersion of the invention to a portion of skin of the mammal, allowing a sufficient amount of water in the aqueous phase to evaporate from the dispersion so as to form a tacky layer on the portion of the skin, and applying the dressing to the said tacky layer on the portion of skin.

The dispersion of the invention is effective for use in delivering a pharmaceutically or cosmetically active ingredient by topical application. A pharmaceutical or cosmetic composition according to the invention comprises an admixture of an aqueous dispersion as described above and a pharmaceutically or cosmetically active ingredient, respectively. A method according to the invention of treating a disease or condition in a mammal in need of such treatment comprises topically applying a therapeutically effective amount of the pharmaceutical or cosmetic composition according to the invention as described above to a portion of skin of the mammal.

The alkenyl-containing organopolysiloxane (a) can be a substantially linear polydiorganosiloxane or a branched organopolysiloxane. Examples of suitable alkenyl groups include vinyl, hexenyl, allyl, isopropenyl or butenyl groups. The bonding position for the alkenyl groups may be, for example, the terminal position and/or a pendant or side chain position on the molecular chain. Preferably the alkenyl-containing organopolysiloxane (a) contains on average at least two vinyl groups per molecule. The organic groups other than alkenyl groups in the alkenyl-containing organopolysiloxane can for example be alkyl groups having 1 to 12 carbon atoms or aryl groups having 6 to 10 carbon atoms. The organic groups other than alkenyl groups can for example be alkyl groups having 1 to 4 carbon atoms, typically methyl or ethyl groups.

One example of a suitable branched alkenyl-containing organopolysiloxane has the structure described in EP1070734. The branched siloxane may consist of (i) one or more units of the formula $(SiO_{4/2})$ and ii) from 15 to 995 units of the formula $Rb_2SiO_{2/2}$ which units (i) and (ii) may be inter-linked in any appropriate combination, and iii) units of the formula $RaRb_2SiO_{1/2}$, wherein each Ra substituent is selected from the group consisting of an alkyl group having from 1 to 6 carbon atoms and an alkenyl group having up to 6 carbon atoms, and each Rb substituent is selected from the group consisting of an alkyl group having from 1 to 6 carbon atoms, an alkenyl group having 2 to 6 carbon atoms, an aryl group, an alkoxy group, an acrylate group and a methacrylate group. At least two substituents in the branched siloxane are alkenyl groups. Preferably at least three substituents in the branched siloxane are alkenyl groups. For example at least three Ra substituents in the branched siloxane can be alkenyl groups.

The alkenyl-containing organopolysiloxane (a) may in an alternative example be an alkenyl-terminated polydiorganosiloxane, for example a vinyl-terminated polydimethylsiloxane. Although such an alkenyl-containing polydiorganosiloxane (a) may contain more than 2, for example 3 up to 6 or more alkenyl groups per molecule, it is often preferred that the alkenyl-containing organopolysiloxane contains only two alkenyl groups per molecule. It may for example be a vinyl-endcapped polydimethylsiloxane of formula $CH_2=CH-Si(CH_3)_2O-[Si(CH_3)_2O]_n-Si(CH_3)_2-CH=CH_2$, wherein n is an average number of from 100 to 10000, preferably from 100 to 1000.

The alkenyl-containing organopolysiloxane (a) preferably has a dynamic viscosity of at least 100 milliPascal-seconds (mPa·s) when tested as described in ASTM D1084-08 Method B (Standard Test Methods for Viscosity of Adhesives) at 25° C.) or ASTM D4287-00(2010) (Standard Test Method for High-Shear Viscosity Using a Cone/Plate Viscometer) at 25° C., and may for example have a dynamic viscosity of from 100 to 100,000,000 mPa·s, particularly 100 to 100,000 mPa·s.

The alkenyl-containing organopolysiloxane can comprise one or more alkenyl-containing organopolysiloxane as described above. For example it may comprise at least one substantially linear polydiorganosiloxane and at least one branched organopolysiloxane.

Optionally the alkenyl-containing organopolysiloxane (a) comprises an alkenyl-containing organopolysiloxane resin, for example a resin comprising at least one $SiO_{4/2}$ unit and triorganosiloxy units selected from $R^1_2R^2SiO_{1/2}$ units and $R^1_3SiO_{1/2}$ units, where $R^1$ represents a $C_{1-10}$ alkyl group and $R^2$ represents an alkenyl group. Each $R^1$ group can for example be methyl, ethyl, propyl, 2 cyclopentyl or cyclohexyl. Each $R^2$ group can for example be vinyl, allyl, isopropenyl, butenyl, hexenyl, or cyclohexenyl, wherein vinyl is preferred. The alkenyl-containing organopolysiloxane resin may for example contain 0.4 to 5.0 mass % alkenyl groups. The alkenyl-containing organopolysiloxane resin can for example comprise 0 to 20 wt % of component (a).

The SiH containing siloxane (b) can for example comprise groups selected from $RHSiO_{2/2}$ groups and $R2HSiO1_{/2}$ groups and optionally $R_2SiO_{2/2}$ groups and/or $R_3SiO_{1/2}$ groups, wherein each R denotes an alkyl or aryl group having no more than 8 carbon atoms. The groups R can for example be alkyl groups having 1 to 4 carbon atoms or phenyl groups, typically methyl groups.

The SiH containing siloxane (b) has an average per molecule of at least 2 SiH moieties. Although the invention includes the use of an alkenyl-containing organopolysiloxane (a) containing only 2 alkenyl groups per molecule with a SiH containing siloxane (b) containing only 2 SiH moieties per molecule, it is preferred that either the alkenyl-containing organopolysiloxane (a) contains more than 2 alkenyl groups per molecule or the SiH containing siloxane (b) contains more than 2 SiH moieties per molecule. If the alkenyl-containing organopolysiloxane (a) contains only 2 alkenyl groups per molecule and the SiH containing siloxane (b) contains only 2 SiH moieties per molecule, they will react together in the presence of a hydrosilylation catalyst to undergo chain extension to form a linear polysiloxane of increased molecular weight and increased viscosity, but will in general not undergo crosslinking or form an elastomeric silicone material. If either the alkenyl-containing organopolysiloxane (a) contains more than 2 alkenyl groups per molecule or the SiH containing siloxane (b) contains more than 2 SiH moieties per molecule, they will react together in the presence of a hydrosilylation catalyst to undergo crosslinking, thereby forming an elastomeric silicone material. Preferably the SiH containing siloxane has an average per molecule of more than 2 SiH moieties, for example from 2.5 to 200 SiH moieties, more preferably 3 to 20 SiH moieties.

The SiH containing siloxane (b) can for example be a poly(methylhydrogensiloxane) or a dimethylsiloxane methylhydrogensiloxane copolymer. The SiH containing siloxane can for example comprise 4 to 200 siloxane units and may be an oligomer having 4 to 20 siloxane units. The SiH containing siloxane can for example have a dynamic viscosity at 25° C. of from 1 to 300 mPa·s.

If it is desired that the elastomeric silicone material should contain pendant groups such as hydrocarbon groups having 2 to 30 carbon atoms or polyoxyalkylene groups, the SiH containing siloxane may be modified to contain such groups. For example a poly(methylhydrogensiloxane) or a dimethylsiloxane methylhydrogensiloxane copolymer can be pre-reacted with a hydrocarbon having 2 to 30 carbon atoms and one terminal alkenyl group, for example a 1-alkene, or with a polyoxyalkylene having one terminal alkenyl group, in the presence of a hydrosilylation catalyst. The molar ratio of alkenyl groups to SiH moieties in such pre-reaction must be sufficiently low that the resulting SiH containing siloxane (b) having pendant groups still contains at least 2, preferably more than 2, SiH moieties per molecule.

The molar ratio of SiH moieties of the SiH containing siloxane (b) to alkenyl groups of the alkenyl-containing organopolysiloxane (a) is preferably in the range from 0.5:1 to 1.5:1, more preferably 0.6:1 to 1.2:1. The weight ratio of the SiH containing siloxane (b) to the alkenyl-containing organopolysiloxane (a) may vary widely depending on the reagents used but in general is in the range 1:1000 to 10:1, particularly in the range of 1:200 to 6:1, and is often in the range 1:500 to 1:5.

Catalysts for catalyzing hydrosilylation reactions are known in the art and are commercially available. Such hydrosilylation catalysts can be a metal selected from platinum, rhodium, ruthenium, palladium, osmium, and iridium. Alternatively, the hydrosilylation catalyst may be a compound of such a metal, for example, chloroplatinic acid, chloroplatinic acid hexahydrate, platinum dichloride, and complexes of said compounds with low molecular weight organopolysiloxanes or platinum compounds microencapsulated in a matrix or core/shell type structure. Complexes of platinum with low molecular weight organopolysiloxanes include 1,3-diethenyl-1,1,3,3-tetramethyldisiloxane complexes with platinum. These complexes may be microencapsulated in a resin matrix. Exemplary hydrosilylation catalysts are described in U.S. Pat. Nos. 3,159,601; 3,220,972; 3,296,291; 3,419,593; 3,516,946; 3,814,730; 3,989,668; 4,784,879; 5,036,117; and 5,175,325 and EP 0 347 895 B. Microencapsulated hydrosilylation catalysts and methods of preparing them are known in the art, as exemplified in U.S. Pat. Nos. 4,766,176 and 5,017,654.

The appropriate amount of the catalyst will depend upon the particular catalyst used and the particular alkenyl-containing organopolysiloxane (a) and SiH containing siloxane (b) used. A platinum-containing catalyst may be present in an amount sufficient to provide at least 2 parts per million (ppm) of platinum based on the total weight of the alkenyl-containing organopolysiloxane (a) and the SiH containing siloxane (b) in the composition. Typically, the platinum is present in an amount sufficient to provide 4 to 150 weight ppm of platinum on the same basis. The catalyst may be added as a single species or as a mixture of two or more different species.

The SiH moieties of the SiH containing siloxane (b) and the alkenyl groups of the alkenyl-containing organopolysiloxane (a) react together in the presence of the hydrosilylation catalyst. The product of the reaction is characterised by links between siloxane chains of the formula

≡Si—CH2-CH(Y)-(A)$a$-Si≡ in which the Si atoms shown each form part of different siloxane chains; a=0 or 1; A if present represents a hydrocarbon linkage usually having 1 to 4 carbon atoms; and Y represents hydrogen or an alkyl group having 1 or 2 carbon atoms. The alkenyl-containing organopolysiloxane (a) and the SiH containing siloxane (b) may be substantially completely reacted so that the reaction product present in the dispersion either contains substantially no unreacted alkenyl groups or contains substantially no unreacted SiH groups (i.e., reacted except for any residual SiH and/or alkenyl that is slow to react for steric hindrance or other reasons), or may be partially reacted.

The polymeric film former can in general be any polymer which is soluble or dispersible in a solution of the surfactant of molecular weight below 1600 and is capable of forming a coherent film when a solution or dispersion of the polymeric film former in an aqueous solution of the surfactant (in the absence of any silicone material) is deposited on a substrate and dried. It may be advantageous that the polymeric film former is soluble in water and/or that the polymeric film former acts as a surface active agent or as an emulsifying agent even in the absence of a surfactant of molecular weight below 1600. Polyvinyl alcohol (PVA) is an example of a polymeric film former which is also an emulsifying agent. Further examples of polymeric film formers which are suitable for use in the present invention include polyethers such as polyethylene oxide and anionic polymers, particularly sulphonate polymers such as polystyrene sulphonate and sulfopolyesters, polyesters, polylactic and polyglycolic acids, polysaccharides, chitosan derivatives, plasticized nitrocellulose, vinylpyrrolidone polymers, polyacrylates, polymethacrylates, polyacrylamides, polyacrylonitriles and polyurethanes. The polymeric film former can be a copolymer. The polymeric film former can be a mixture of two or more of the above polymers.

The PVA can in general be any PVA useful for dispersing the alkenyl-containing organopolysiloxane (a) and the SiH containing siloxane (b) and may be any commercially available polyvinyl alcohol and may for example have a degree of hydrolysis in the range 80% to 99.9%, preferably 85% to 99%. The viscosity of the PVA, measured as the viscosity of a 4% aqueous solution at 20° C. determined by Hoppler viscometer (DIN 53015), can for example be in the range 3 to 60 mPa·s. Various suitable PVAs are sold by Kuraray America Inc. under the trade mark 'Mowiol', for example Mowiol 18-88, Mowiol 8-88, Mowiol 30-88, Mowiol 30-92 and Mowiol 20-98. Various suitable PVAs are also available from DuPont Inc. under the trade mark 'Elvanol'.

Suitable polyethylene oxides are sold under the trade mark 'Polyox', for example Polyox WSR205, Polyox WSR301, Polyox WSR308, Polyox WSRn10, Polyox WSRn12k and Polyox WSRn10k.

A suitable polystyrene sulphonate is sodium polystyrene sulfonate which is for example sold under the trade mark 'Flexan II'.

Examples of suitable polyesters include any water-soluble polyester like polyester-5, or a water-soluble sulfopolyester such as those sold under the trademarks Eastman AQ™ 38S polymer, Eastman AQ™ 55S polymer, Eastman AQ™ 48 polymer.

Examples of suitable polysaccharides include starch, modified starch and cellulose esters and ethers such as cellulose acetate, cellulose acetate butyrate, sodium carboxymethylcellulose or hydroxyethyl cellulose, chitin, nitrocellulose, callose, chrysolaminarin, xylan, arabinoxylan, mannan, fucoidan and galactomannan. Examples are sold under the trade names Amaze (modified starch), Amaze XT (dehydroxanthan gum), Methocel, Ethocel and Natrosol (cellulose ethers).

Examples of suitable vinylpyrrolidone polymers include polyvinylpyrrolidone and vinylpyrrolidone co polymers, for example copolymers with styrene, hexadecene, acrylamide, acrylate, methacrylate, vinylalcohol, vinyl acetate, vinyl caprolactam, acrylic or methacylic acid sold for example under the trade names 'Luvitec', 'Luviskol' or Antaron-Ganex®.

Examples of suitable polyacrylates, polymethacrylates and acrylate copolymers include copolymers of acrylates and/or methacrylates with acrylamide sold for example 'Dermacryl' as example Dermacryl 79 or Dermacryl C, 'Avalure' as example Avalure™ AC 120, and 'Luvimer' as example Luvimer 30E.

Examples of suitable polyurethanes and copolymers include polyurethane-34 and 35 sold under the trade names 'Baycusan®' and 'Avalure™ UR'. Polyurethane-34 is a complex polymer that is formed in a multi-step reaction. A copolymer of hexanediol, neopentyl glycol, and adipic acid is reacted with hexamethylene diisocyanate. The resulting polymer is further reacted with N-(2-aminoethyl)-3-aminoethanesulfonic acid and ethylenediamine. Polyurethane-35 is a copolymer of adipic acid, dicyclohexylmethane diisocyanate, ethylenediamine, hexanediol, neopentyl glycol and sodium N-(2-aminoethyl)-3-aminoethanesulfonate.

The surfactant of molecular weight below 1600 can be a cationic, anionic, nonionic or amphoteric surfactant.

Examples of suitable non-ionic surfactants include polyoxyalkylene alkyl ethers such as condensates of ethylene oxide with long chain fatty alcohols or fatty acids such as a $C_{4-16}$ alcohol, particularly polyethylene glycol long chain (12-14C) alkyl ethers, condensates of ethylene oxide with an amine or an amide, condensation products of ethylene and propylene oxide, esters of glycerol, sucrose, sorbitol, fatty acid alkylol amides, sucrose esters, fluoro-surfactants, fatty amine oxides, polyoxyalkylene sorbitan ethers, polyoxyalkylene alkoxylate esters, and polyoxyalkylene alkylphenol ethers.

Examples of cationic surfactants include quaternary ammonium salts, for example halides such as octyl trimethyl ammonium chloride, dodecyl trimethyl ammonium chloride, hexadecyl trimethyl ammonium chloride, octyl dimethyl benzyl ammonium chloride, decyl dimethyl benzyl ammonium chloride, didodecyl dimethyl ammonium chloride, dioctadecyl dimethyl ammonium chloride, tallow trimethyl ammonium chloride and coco trimethyl ammonium chloride, fatty amines and fatty acid amides and their derivatives, basic pyridinium compounds, quaternary ammonium bases of benzimidazolines and polypropanolpolyethanol amines.

Examples of anionic surfactants include alkyl benzene sulphonic acids and their salts, for example sodium dodecylbenzenesulfonate, and alkyl sulphonic acids and their salts, alkyl sulphates, alkyl ether sulphates, fatty acid ester sulphates, alkyl sulfosuccinates, acyl sarcosinates, alkyl carboxylates, fatty acids, and phosphate esters in acid or salt form.

The surfactant of molecular weight below 1600 can in general be used in an amount such that the weight ratio of polymeric film former to non-polymeric surfactant is below 2.5:1, for example in the range 0.1:1 to 2:1, particularly 0.3:1 to 1.5:1. The surfactant can conveniently be added to the mixture of alkenyl-containing organopolysiloxane (a) and SiH containing siloxane (b) with the aqueous polymeric film former solution before emulsification but can be added to the aqueous silicone emulsion after emulsification.

In the first step of the process of the invention, the alkenyl-containing organopolysiloxane (a) and the SiH containing siloxane (b) are mixed together in the absence of any hydrosilylation catalyst. The alkenyl-containing organopolysiloxane (a) and the SiH containing siloxane (b) are both generally liquids. The resulting liquid mixture is then emulsified in an aqueous solution of polymeric emulsifying agent and non-polymeric surfactant to form an aqueous silicone emulsion in which liquid droplets of the mixture of alkenyl-containing organopolysiloxane (a) and SiH containing siloxane (b) are dispersed in a continuous aqueous phase which is a solution of the polymeric emulsifying agent and non-polymeric surfactant.

The concentration of polymeric emulsifying agent in the aqueous solution into which the mixture of alkenyl-containing organopolysiloxane (a) and SiH containing siloxane (b) is emulsified can for example be 2 to 40% by weight polymeric emulsifying agent, preferably 5 to 30%, based on the weight of the aqueous solution. The amount of aqueous solution of polymeric emulsifying agent and non-polymeric surfactant into which the mixture of alkenyl-containing organopolysiloxane (a) and SiH containing siloxane (b) is emulsified can for example be 2 to 100% by weight based on the weight of the mixture of alkenyl-containing organopolysiloxane (a) and SiH containing siloxane (b). The amount of aqueous solution of polymeric emulsifying agent and non-polymeric surfactant is preferably 4 to 50% based on the weight of the mixture of alkenyl-containing organopolysiloxane (a) and SiH containing siloxane (b), more preferably 5 to 40%. The amount of polymeric emulsifying agent thereby mixed in forming the emulsion is preferably in the range from 1.2% to 20% by weight polyvinyl alcohol based on the weight of the mixture of alkenyl-containing organopolysiloxane (a) and SiH containing siloxane (b), more preferably 1.5 to 15% polymeric emulsifying agent based on the weight of the mixture of alkenyl-containing organopolysiloxane (a) and SiH containing siloxane (b).

At low ratios of aqueous solution of polymeric emulsifying agent and non-polymeric surfactant to polysiloxane mixture, for example below 15% by weight aqueous solution of polymeric emulsifying agent and non-polymeric surfactant based on the weight of the mixture of alkenyl-containing organopolysiloxane (a) and SiH containing siloxane (b), a non-Newtonian "thick phase" is formed, which is much more viscous at low shear rate (below $0.1 \text{ s}^{-1}$) than the silicone polymer alone and often exhibits a yield stress (viscoplastic behaviour). Formation of such a thick phase allows more thorough mixing of the hydrophobic siloxane reagents with the aqueous phase and thus aids in the formation of the emulsion. In the initial stage of the emulsification, the amount of aqueous solution of polymeric emulsifying agent and non-polymeric surfactant to polysiloxane mixture may be below 15% as defined above for formation of a thick phase. Such a thick phase can for example contain 2 to 10% by weight aqueous solution of polymeric emulsifying agent and non-polymeric surfactant based on the weight of the mixture of alkenyl-containing organopolysiloxane (a) and SiH containing siloxane (b). Optionally only a part of the polymeric emulsifying agent and/or only a part of the non-polymeric surfactant is used in the initial stage of the emulsification. The thick phase can be diluted with water or with further solution of polymeric emulsifying agent and/or non-polymeric surfactant to form a less viscous emulsion. The concentration of the mixture of alkenyl-containing organopolysiloxane (a) and SiH containing siloxane (b) in the resulting emulsion, diluted if required, can for example be in the range 25 to 90% by weight based on the total weight of the emulsion, typically 40 to 80% based on the total weight of the emulsion.

Emulsification is generally carried out in a high shear mixer, for example a rotor and stator mixer. The particle size of the emulsion can be reduced in a subsequent step if desired, for example in an apparatus applying increased shear such as a homogeniser or microfluidiser, or a sonolator (ultrasonic mixer), producing an emulsion in which the volume median diameter of the droplets is in the range 0.3 to 30 µm (micrometers).

The alkenyl-containing organopolysiloxane (a) and the SiH containing siloxane (b) can if desired be mixed before emulsification with an excipient oil. By an 'oil' we mean a liquid which is immiscible with water. The excipient oil should be miscible with the mixture of alkenyl-containing organopolysiloxane (a) and SiH containing siloxane (b). The excipient oil generally contains no functional groups which are reactive with the alkenyl groups of alkenyl-containing organopolysiloxane (a) or the SiH groups of SiH containing siloxane (b) under the conditions of emulsification. The oil may for example be a softener or plasticiser for the elastomeric silicone that is to be formed, or may be an oil having benefit in skin care, for example as an emollient. The oil may be an excipient for a pharmaceutically or cosmetically active material that is to be incorporated into the silicone dispersion; the oil may be a mixture of such an excipient and a pharmaceutically or cosmetically active material. The amount of such an oil mixed before emulsification can be up to 50% by weight based on the weight of the alkenyl-containing organopolysiloxane (a) and the SiH containing siloxane (b), for example 1 to 40% and preferably 2 to 20% by weight based on the weight of the alkenyl-containing organopolysiloxane (a) and the SiH containing siloxane (b).

The hydrosilylation catalyst is preferably added to the emulsion simultaneously with the polymeric emulsifying agent and/or the non-polymeric surfactant, although the catalyst can be added to the emulsion after emulsification if desired. Most preferably the hydrosilylation catalyst is added to the emulsion simultaneously with the polymeric emulsifying agent and the non-polymeric surfactant, for example by mixing the catalyst into the aqueous solution of polymeric emulsifying agent and non-polymeric surfactant before emulsification. When the catalyst contacts the mixture of alkenyl-containing organopolysiloxane (a) and SiH containing siloxane (b), reaction of the alkenyl groups of (a) with the SiH moieties of (b) is initiated. Polymerisation of the alkenyl-containing organopolysiloxane (a) and SiH containing siloxane (b) thus takes place within the liquid disperse phase of the emulsion (emulsion polymerisation). Polymerisation takes place at ambient temperature in the presence of the hydrosilylation catalyst. Ambient temperature polymerisation may be preferred for convenience, although any temperature in the range 0 to 100° C. can be used. An elevated temperature, for example in the range 50 to 100° C., may be preferred to give more rapid polymerisation.

It may be preferred that the pH of the dispersion is below pH6, more particularly below pH5. This avoids the possibility of hydrolysis of PVA in the presence of a platinum catalyst so that the dispersion remains stable on storage and retains its properties such as the mechanical properties and contact angle of a film deposited from the dispersion. A buffering agent such as citric acid with sodium hydroxide can be added to the emulsion to control the pH to the desired value.

A pharmaceutically or cosmetically active material, optionally in admixture with an excipient, can be added to the emulsion at any time after emulsification. The amount of pharmaceutically or cosmetically active material, including any excipient, can be up to 50% by weight based on the weight of the alkenyl-containing organopolysiloxane (a) and the SiH containing siloxane (b), for example 1 to 40% and preferably 2 to 20% by weight based on the weight of the alkenyl-containing organopolysiloxane (a) and the SiH containing siloxane (b).

A filler can be added to the emulsion at any time after emulsification. A filler can for example be a reinforcing filler such as hydrophilic silica, silica treated to be hydrophobic or a carbonate such as calcium carbonate. A filler can alternatively be a cosmetic filler, for example a silicone crosspolymer powder with silica treated coating or a silicone elastomer powder. The filler can be added as a particulate solid or can be added as a suspension, for example a nonionic aqueous suspension of a silicone elastomer powder.

The composition of the aqueous silicone dispersion of the invention thus comprises 5 to 90% by weight of the alkenyl-containing organopolysiloxane (a); 0.025 to 75% by weight of the SiH containing siloxane (b); 0.0002 to 0.02% by weight of the hydrosilylation catalyst; 0.3 to 18% by weight PVA; 0.04 to 18% by weight nonpolymeric surfactant; 8 to 94% by weight water; and optionally 0 to 50% by weight water immiscible oil which is miscible with but not reactive with the alkenyl-containing organopolysiloxane (a) or the SiH containing siloxane (b); and/or 0 to 50% by weight pharmaceutically or cosmetically active material including any excipient therefore.

A "pharmaceutically active" material means any compound or mixtures of compounds that provide a pharmaceutical or medical benefit. Thus, pharmaceutically active materials include materials consider as an active ingredient or active drug ingredient as generally used and defined by the United States Department of Health & Human Services Food and Drug Administration, contained in Title 21, Chapter I, of the Code of Federal Regulations, Parts 200-299 and Parts 300-499. A 'cosmetically active' material means any compound or mixtures of compounds that are additives in personal care formulations added for the purpose of treating hair or skin to provide a cosmetic and/or aesthetic benefit.

The pharmaceutically active material can include any component that is intended to furnish pharmacological activity or other direct effect in the diagnosis, cure, mitigation, treatment, or prevention of disease, or to affect the structure or any function of the body of a human or other animals. The pharmaceutically active material can include those components that may undergo chemical change in the manufacture of drug products and be present in drug products in a modified form intended to furnish the specified activity or effect.

Some representative examples of pharmaceutically active materials include drugs, vitamins, minerals; hormones; topical antimicrobial agents such as antibiotic active ingredients, antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

Examples of cosmetically active materials include emollients, waxes, moisturizers, sebum absorbants or sebum control agents, vegetable or botanical extracts, pigments, colorants, conditioning agents, UV absorbers and sunscreen agents, proteins and amino-acids and their derivatives, fragrances, antiperspirants, colour care additives, pearlising agents, antioxidants, skin bleaching agents and skin protectants.

Examples of vitamins include a variety of different organic compounds such as alcohols, acids, sterols, and quinones. They may be classified into two solubility groups: lipid-soluble vitamins and water-soluble vitamins. Lipid-soluble vitamins that have utility in personal care formulations include retinol (vitamin A), ergocalciferol (vitamin D2), cholecalciferol (vitamin D3), phytonadione (vitamin K1), and tocopherol (vitamin E). Water-soluble vitamins that have utility in personal care formulations include ascorbic acid (vitamin C), thiamin (vitamin B1) niacin (nicotinic acid), niacinamide (vitamin B3), riboflavin (vitamin B2), pantothenic acid (vitamin B5), biotin, folic acid, pyridoxine (vitamin B6), and cyanocobalamin (vitamin B12). Additional examples of vitamins include derivatives of vitamins such as retinyl palmitate (vitamin A palmitate), retinyl acetate (vitamin A acetate), retinyl linoleate (vitamin A linoleate), and retinyl propionate (vitamin A propionate), tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxylated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), sodium tocopheryl phosphate, ascorbyl palmitate, ascorbyl dipalmitate, ascorbyl glucoside, ascorbyl tetraisopalmitate, tetrahexadecyl ascorbate, ascorbyl tocopheryl maleate, potassium ascorbyl tocopheryl phosphate or tocopheryl nicotinate.

The pharmaceutically active material used in processes according to the invention can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole, clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids. Active drug ingredients for purposes of the present invention also include antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; agents for the treatment of central nervous system diseases such as Parkinson's, or Alzheimer's; and antidermatitis agents.

The pharmaceutically active material can be a protein, such as an enzyme. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozyrnes, superoxide dismutase, catalase, and mixtures thereof. Said protease include, but are not limited to, trypsin, chymotrypsin, pepsin, pancreatin and other mammalian enzymes; papain, bromelain and other botanical enzymes; subtilisin, epidermin, nisin, naringinase(L-rhammnosidase) urokinase and other bacterial enzymes. Said lipase include, but are not limited to, triacyl-glycerol lipases, monoacyl-glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

The pharmaceutically or cosmetically active material may be a sunscreen agent. The sunscreen agent can be selected from any sunscreen agent known in the art to protect skin from the harmful effects of exposure to sunlight. The sunscreen compound is typically chosen from an organic compound, an inorganic compound, or mixtures thereof, that absorbs ultraviolet (UV) light. UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)]aminobenzoate, glyceryl aminobenzoate, homosalate, lawsone with dihydroxyacetone, menthyl anthranilate, octocrylene, ethyl hexyl methoxycinnamate, octyl salicylate, oxybenzone, padimate O, phenylbenzimidazole sulfonic acid, red petrolatum, sulisobenzone, titanium dioxide, and trolamine salicylate. Further examples of UV absorbers are acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic Acid, benzyl salicylate, bornelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, triPABA panthenol, urocanic acid, and VA/crotonates/methacryloxybenzophenone-1 copolymer.

The cosmetically active material may be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Many of these perfume ingredients are described in detail in standard textbook references such as *Perfume and Flavour Chemicals,* 1969, S. Arciander, Montclair, N.J. Fragrances may be exemplified by, but not limited to, perfume ketones and perfume aldehydes. Illustrative of the perfume ketones are buccoxime; iso jasmone; methyl beta naphthyl ketone; musk indanone;

tonalid/musk plus; Alpha-Damascone, Beta-Damascone, Delta-Damascone, Iso-Damascone, Damascenone, Damarose, Methyl-Dihydrojasmonate, Menthone, Carvone, Camphor, Fenchone, Alpha-ionone, Beta-Ionone, Gamma-Methyl so-called Ionone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or Livescone, 6-Isopropyl-decahydro-2-naphtone, Dimethyl-Octenone, Freskomenthe, 4-(1-Ethoxyvinyl)-3,3,5,5-tetramethyl-Cyclohexanone, Methyl-Heptenone, 2-(2-(4-Methyl-3-cyclohexen-1-yl)propyl)-cyclopentanone, 1-(p-Menthen-6(2)-yl)-1-propanone, 4-(4-Hydroxy-3-methoxyphenyl)-2-butanone, 2-Acetyl-3,3-Dimethyl-Norbomane, 6,7-Dihydro-1,1,2,3,3-Pentamethyl-4(5H)-Indanone, 4-Damascol, Dulcinyl or Cassione, Gelsone, Hexalon, Isocyclemone E, Methyl Cyclocitrone, Methyl-Lavender-Ketone, Orivon, Para-tertiary-Butyl-Cyclohexanone, Verdone, Delphone, Muscone, Neobutenone, Plicatone, Veloutone, 2,4,4,7-Tetramethyl-oct-6-en-3-one, and Tetrameran. Examples of perfume aldehydes are adoxal; anisic aldehyde; cymal; ethyl vanillin; florhydral; helional; heliotropin; hydroxycitronellal; koavone; lauric aldehyde; lyral; methyl nonyl acetaldehyde; P.T. bucinal; phenyl acetaldehyde; undecylenic aldehyde; vanillin; 2,6,10-trimethyl-9-undecenal, 3-dodecen-1-al, alpha-n-amyl cinnamic aldehyde, 4-methoxybenzaldehyde, benzaldehyde, 3-(4-tert butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)]-decylidene-8)-butanal, octahydro-4,7-methano-1H-indenecarboxaldehyde, 3-ethoxy-4-hydroxy benzaldehyde, para-ethyl-alpha, alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methyl pentyl)-3-cylohexene-1-carboxaldehyde, 7-methoxy-3,7-dimethyloctan-1-al, 2-methyl undecanal, 2-methyl decanal, 1-nonanal, 1-octanal, 2,6,10-trimethyl-5,9-undecadienal, 2-methyl-3-(4-tertbutyl)propanal, dihydrocinnamic aldehyde, 1-methyl-4-(4-methyl-3-pentenyl)-3-cyclohexene-1-carboxaldehyde, 5 or 6 methoxyl 0 hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl-octanal, trans-4-decenal, 2,6-nonadienal, paratolylacetaldehyde; 4-methylphenylacetaldehyde, 2-methyl-4-(2,6,6-trimethyl-1-cyclohexen-1-yl)-2-butena 1, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyl octanal, alpha-methyl-4-(1-methyl ethyl) benzene acetaldehyde, 6,6-dimethyl-2-norpinene-2-propionaldehyde, para methyl phenoxy acetaldehyde, 2-methyl-3-phenyl-2-propen-1-al, 3,5,5-trimethyl hexanal, Hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, hexanal, trans-2-hexenal, 1-p-menthene-q-carboxaldehyde, hexyl cinnamic aldehyde and mixtures thereof. Further examples of fragrances or perfumes include methyl-2-n-hexyl-3-oxo-cyclopentane carboxylate; gamma-dodecalactone; methylphenylcarbinyl acetate; 4-acetyl-6-tert-butyl-1,1-dimethyl indane; patchouli; olibanum resinoid; labdanum; vetivert; copaiba balsam; fir balsam; methyl anthranilate; geraniol; geranyl acetate; linalool; citronellol; terpinyl acetate; benzyl salicylate; phenoxyethyl isobutyrate; cedryl acetal; aubepine; and ethylene brassylate.

Examples of vegetable or botanical extracts are derived from plants (herbs, roots, flowers, fruits, or seeds) in oil or water soluble form, such as coconut, green tea, white tea, black tea, horsetail, sunflower, wheat germ, olive, grape, pomegranate, apricot, carrot, tomato, tobacco, bean, potato, adzuki bean, *catechu*, orange, cucumber, avocado, watermelon, banana, lemon, palm, dill, horseradish, oats, neem, beet, broccoli, pumpkin, soybean, barley, walnut, flax, *ginseng*, poppy, avocado, pea or sesame extract.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as C30-45 Alkyl Methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexadecane; branched $C_8$-$C_{16}$ esters; isohexyl neopentanoate; ester oils such as isononyl isononanoate, cetostearyl octanoate, isopropyl myristate, palmitate derivatives, stearate derivatives, isostearyl isostearate and the heptanoates, octanoates, decanoates or ricinoleates of alcohols or of polyalcohols, or mixtures thereof; oils of plant origin, such as wheatgerm, sunflower, grapeseed, castor, shea, avocado, olive, soybean, sweet almond, palm, rapeseed, cotton seed, hazelnut, macadamia, jojoba, blackcurrant, or evening primrose oil; triglycerides of caprylic/capric acids; or higher fatty acids, such as oleic acid, linoleic acid or linolenic acid.

Examples of waxes include beeswax, lanolin wax, rice wax, carnauba wax, candelilla wax, and hydrocarbon waxes such as microcrystalline waxes, paraffins, ozokerite, polyethylene waxes.

Examples of moisturizers include lower molecular weight aliphatic diols such as propylene glycol and butylene glycol; polyols such as glycerine and sorbitol; and polyoxyethylene polymers such as polyethylene glycol 200; and hyaluronic acid and its derivatives.

Examples of sebum absorbants or sebum control agents include silica silylate, silica dimethyl silylate, dimethicone/vinyl dimethicone crosspolymer, polymethyl methacrylate, cross-linked methylmethacrylate and aluminum starch octenylsuccinate.

Examples of conditioning agents include silicone conditioning agents such as silicone oils, silicone gums and mixtures thereof; organomodified silicone oils, such as amodimethicone, aminopropyl phenyl trimethicone, phenyl trimethicone, trimethyl pentaphenyl trisiloxane, silicone quaternium-16/glycidoxy dimethicone crosspolymer, silicone quaternium-16 and mixtures thereof. Further examples of conditioning agents are cationic conditioning agents including guar derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality.

Proteins or amino-acids and their derivatives suitable for use as cosmetically active materials include proteins extracted from wheat, soy, rice, corn, keratin, elastin or silk and amino-acids derived therefrom. The protein may be in the hydrolyzed form. The protein may be quaternized.

Some examples of antioxidants suitable for use as cosmetically active materials are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, *Camellia sinensis* Oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (*Melaleuca aftemifolia*) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, and zinc dibutyldithiocarbamate.

An example of a skin bleaching agent is hydroquinone. Some examples of skin protectants are allantoin, aluminium acetate, aluminium hydroxide, aluminium sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, and zinc oxide.

An excipient used with such a pharmaceutically or cosmetically active material is generally selected from organic liquids (oils and solvents), silicones and mixtures of these. Many of the liquid organic and silicone materials listed above as emollients are also suitable as excipients for pharmaceutically or cosmetically active materials. Organic liquids suitable as excipients are exemplified by, but not limited to, aromatic hydrocarbons, aliphatic hydrocarbons, alcohols, aldehydes, ketones, amines, esters, ethers, glycols, glycol ethers, alkyl halides and aromatic halides. Hydrocarbons include, isododecane, isohexadecane, Isopar L (C11-C13), Isopar H (C11-C12) and other mineral oils, petrolatum and hydrogenated polydecene. Ethers and esters include, isodecyl neopentanoate, neopentylglycol heptanoate, glycol distearate, dicaprylyl carbonate, dicaprylyl ether, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, isopropyl myristate, isopropyl palmitate, isopropyl isostearate, propylene glycol dicaprylate/dicaprate, caprylic/capric triglyceride and octyl palmitate. Examples of alcohols include glycerol, ethanol, pentylene glycol and propylene glycol. Additional organic carrier fluids suitable as an ingredient of the excipient include fats, oils, fatty acids, and fatty alcohols.

The excipient may be a low viscosity organopolysiloxane having a viscosity at 25° C. in the range of 1 to 1,000 mPa·s such as decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3,bis{(trimethlylsilyl)oxy}trisiloxane pentamethyl{(trimethylsilyl)oxy}cyclotrisiloxane as well as polydimethylsiloxanes, polydiethylsiloxanes, polymethylethylsiloxanes, polymethylphenylsiloxanes, or polydiphenylsiloxanes.

A tacky silicone layer can be formed by coating the aqueous silicone dispersion of the invention on a substrate and drying the layer by allowing water in the aqueous phase of the dispersion to evaporate from the coating on the substrate. The tackiness of the silicone layer produced on drying the dispersion according to the invention can be evaluated by a texturometer.

The substrate can be any material which is not dissolved or otherwise damaged by the aqueous silicone dispersion. The substrate is usually a material which requires adhesion to another material. Examples of substrates include polymeric materials including organic polymers such as polyesters, polyurethanes, polyolefins, vinyl polymers, siloxane polymers, glass, metal, natural and synthetic fibres and textile materials made therefrom, paper and board, wood and ceramic materials. The substrate can for example be a material such as a textile material intended for use as a dressing for a mammal having a wound or skin condition in need of a dressing. A surface of the dressing can be coated with an effective amount of the aqueous dispersion of the invention. A sufficient amount of water in the aqueous phase is allowed to evaporate from the coating on the substrate so as to form a tacky layer on the dressing. The tacky layer on the dressing is then applied to a portion of skin of the mammal to adhere the dressing to the mammal.

The substrate can alternatively be the skin of a mammal, either for adhering a dressing or other material to the skin or for topical application of pharmaceutically or cosmetically active material. An effective amount of the dispersion of the invention can be topically applied to a portion of skin of the mammal. A sufficient amount of water in the aqueous phase is allowed to evaporate from the dispersion so as to form a tacky layer on the portion of the skin. A dressing can then be adhered to the said tacky layer on the portion of skin. A pharmaceutical or cosmetic composition comprising an admixture of the aqueous silicone dispersion and a pharmaceutically or cosmetically active ingredient, respectively, can be used to treat a disease or condition in a mammal in need of such treatment by topically applying a therapeutically effective amount of the composition to a portion of skin of the mammal.

The tacky silicone layer produced according to the invention is preferably crosslinked to an elastomeric silicone material, by reaction of the alkenyl-containing organopolysiloxane (a) and the SiH containing siloxane (b) in the disperse phase of the dispersion in the presence of the hydrosilylation catalyst. The aqueous silicone dispersion of the invention is thus a 1-part silicone elastomer emulsion that forms a tacky layer upon drying after deposition. A hydrosilylation reaction takes place within the disperse phase to form a soft elastomer. Upon drying, a tacky layer is formed without the need of further reaction, partly because the elastomeric silicone disperse phase droplets are soft enough to adhere together. A further benefit of the aqueous silicone dispersion of the invention is that only a low amount of platinum catalyst is required, as the hydrosilylation reaction takes place within the disperse phase and a fast cure is not required for film formation.

The aqueous silicone dispersion of the invention can be used in pharmaceutical and cosmetic treatment in a variety of ways for delivering a pharmaceutically or cosmetically active ingredient to a patient by topical application. A pharmaceutical or cosmetic composition comprising an admixture of the aqueous silicone dispersion and a pharmaceutically or cosmetically active ingredient, respectively, can be deposited as a layer on a backing material to form a dressing. The resulting dressing can be used to treat a disease or condition in a mammal in need of such treatment by topically applying the dressing to a portion of skin of the mammal with a therapeutically effective amount of the layer containing the pharmaceutically or cosmetically active material in contact with the skin. The pharmaceutically or cosmetically active ingredient is absorbed from the layer on the dressing onto and through the skin of the mammal. Alternatively a therapeutically effective amount of a pharmaceutical or cosmetic composition comprising an admixture of the aqueous silicone dispersion and a pharmaceutically or cosmetically active ingredient can be used to treat a disease or condition in a mammal in need of such treatment by topically applying the composition to a portion of skin of the mammal. The composition forms a tacky layer on the skin of the mammal from which the pharmaceutically or cosmetically active ingredient is absorbed onto and through the skin. The tacky layer can be covered by a dressing if desired.

Personal care compositions in which the dispersion of the invention can be used to deliver a cosmetically active ingredient include skin care compositions, hair care compositions and nail care compositions. Skin care compositions include shower gels, soaps, hydrogels, creams, lotions, balms, foundations, lipsticks, eyeliners, blushes, primer, concealer, correctors and pencils. The benefits of using the silicone aqueous dispersion of the invention in skin care compositions may include skin hydration, protection, long lasting, skin adhesion, SPF (sun protection factor) boosting, wash off resistance, tensing, and/or tightening. Hair care compositions include shampoos, conditioners, gels, pomades, cuticle coats, serum, sprays, colouring products and mascaras. The benefits of using the silicone aqueous dispersion in hair care compositions may include improved styling, fixative, conditioning, color retention and/or anti-frizz, and the benefits of using the silicone aqueous dispersion on eyelashes may include thickening, water resistance, and/or eyelash lengthening (extension). Nail care compositions include color coats, base coats, nail hardeners. The benefits of using the silicone aqueous dispersion in nail care compositions may include improved protection, long lasting effect, scratch resistance and/or adhesion. The aqueous silicone dispersion of the invention can be formulated into an oil in water cosmetic formulation or into a water in oil cosmetic formulation.

Health care compositions in which the dispersion of the invention can be used to deliver a pharmaceutically active ingredient include patches, creams, unguents, sticks, sprays and medicated nail varnish.

The invention is illustrated by the following Examples, in which parts and percentages are by weight unless otherwise stated.

EXAMPLE 1

Example 1: 49.52% of a branched siloxane of a structure described in EP1070734 comprising $SiO_{4/2}$ units, dimethylsiloxane units and dimethylvinylsilyl units, with a viscosity of 150 mPa·s, a degree of polymerization of 120 and 1.16 wt % of vinyl functions was mixed with 10.27% of a linear hydride functional siloxane oligomer of 10 mPa·s containing 0.18 wt % of hydride functions in a 500 ml glass bottle with a 4-blades propeller at 250 rpm for 1 min. 1.53% of a polyoxyethylene (6) tridecyl ether, as nonionic surfactant, and 4.99% of a 10% active solution of 'Mowiol 30-88' PVA of viscosity 30CP (measured as the viscosity of a 4% aqueous solution at 20° C. determined by Hoppler viscometer (DIN 53015)), and a hydrolysis level of 88%, are both added to the above silicone mixture and mixed for 5 min at 250 rpm. 33.0% of deionized water is then added to the above mixture under stirring at maximum speed (24000 rpm) with an Ultraturrax® T25 basic high shear mixer equipped with a dispersing element S25 KV for 1 min 30 secs. An emulsion is formed and then 0.7% of an emulsion of Syloff 4000 catalyst (providing 4 ppm of Pt) was added.

Hydrosilylation proceeded in the emulsion. The aqueous silicone dispersion produced was coated using a stainless steel coating bar at a thickness of 90 um on a Mylar® polyester release liner. The coated aqueous silicone dispersion was then dried at room temperature for 15 min to form an adhesive silicone layer. The laminate hence produced is cut in smaller strips of 19.5 cm×6.5 cm.

The tackiness of the silicone layer produced was evaluated by a TA.XT plus Texture Analyser from Stable Macro Systems equipped with a multiple indexing plate. One strip of laminate produced as described above is placed within 2 multiple indexing plastic plates. Each plastic plate has a dimension of 19.5 cm×14 cm and has 7 holes of a diameter of 1.5 cm located in the middle of the plate. The system formed has a bottom plate in contact with the uncoated side of the strip and an upper plate in contact with the coated side of the strip. A 7 mm domical probe (P/7D) is brought down in contact with the silicone layer using a 5 kg load cell (calibrated with 2 kg), stays in contact for 10 seconds and goes up again at 1.1 mm/s. The maximum force required to release the probe from the silicone layer (kg) is measured. Each strip being measured 7 times, the average maximum force of the strip is recorded in Table 1. This force represents the tackiness of the silicone film. The higher the force the stickier (tackier) the silicone film.

The maximum release force as a tackiness value was confirmed by a parallel assessment of the degree of tackiness by finger touch. The laminates were touched with the finger by 2 persons who ranked the degree of tackiness of the silicone film between 0 and 3; 0 being non-tacky and 3 very tacky. The degrees of tackiness assessed are indicated in Table 1 and were in agreement with the maximum release force as measures of tackiness.

EXAMPLES 2 TO 4

Example 1 was repeated using increasing amounts of the 10% active solution of PVA 30-88 as shown in Table 1. The amount of deionised water added is adjusted so that the total of all materials used reaches 100%

TABLE 1

| | PVA 30-88 solution (wt %) | polyoxyethylene (6) tridecyl ether (wt %) | Active polymer/ Active surfactant (wt %) | Force max (Kg) | Degree of tackiness |
|---|---|---|---|---|---|
| Example 1 | 4.99 | 1.53 | 0.33 | 0.175 | 3 |
| Example 2 | 10.02 | 1.53 | 0.65 | 0.113 | 2 to 3 |
| Example 3 | 15.1 | 1.68 | 0.90 | 0.092 | 2 |
| Example 4 | 19.92 | 1.53 | 1.30 | 0.086 | 2 |

As shown in Table 1, in the Examples 1 to 4, it is possible to decrease the level of tackiness of the silicone film by increasing the content of PVA 30-88 solution within the aqueous silicone dispersion; the highest the content of PVA 30-88 solution in the aqueous silicone dispersion, the less tacky the silicone film formed.

EXAMPLE 5 TO 7

Example 1 was repeated with 10.85 wt % of the linear hydride functional siloxane oligomer of 10 mPa·s containing 0.18 wt % of hydride functions and varying amounts of polyoxyethylene (6) tridecyl ether, as nonionic surfactant. 1.03, 3 and 4.5 wt % of polyoxyethylene (6) tridecyl ether were respectively used in Examples 5, 6, and 7. Results are shown in Table 2

TABLE 2

| | PVA 30-88 solution (wt %) | polyoxyethylene (6) tridecyl ether (wt %) | Active PVA/Active surfactant (wt %) | Force max (Kg) |
|---|---|---|---|---|
| Example 5 | 15.07 | 1.03 | 1.46 | 0.040 |
| Example 6 | 15.10 | 3.0 | 0.51 | 0.068 |
| Example 7 | 15.09 | 4.5 | 0.34 | 0.036 |

EXAMPLE 8

Example 1 was repeated except that the PVA solution was replaced by 15.11% of an aqueous solution of Flexan II sodium polystyrene sulfonate at 5 wt % active. The emulsion is coated on polyester release liner and the Force max measured as described in Example 1. The Force Max measured is 0.062 kg indicated that the PVA can be replaced by Flexan II.

EXAMPLES 9 TO 15

Example 1 was repeated except that the PVA solution was replaced by 15.07% of an aqueous solution of various grades of Polyox® polyethylene oxide. Example 9 used Polyox WSR308 at 1% of active and Examples 10 to 15 respectively used WSR205, WSR-N10, WSR-N750, WSR-N12K, WSR301, WSR-N10K at 5% of active.

The aqueous silicone dispersions produced were coated using a stainless steel coating bar at a thickness of 90 μm on a polyurethane film. The coated aqueous silicone dispersions were then dried at room temperature for 15 min to form an adhesive silicone layer. The laminate hence produced was cut in smaller strips of 19.5 cm×6.5 cm. The maximum force was measured as described in Example 1 and the results are listed in Table 3. The degree of tackiness of each silicone layer was also assessed by finger touch as described in Example 1 and the results are listed in Table 3.

The aqueous silicone dispersion produced in Example 3 was also coated at a thickness of 90 μm on polyurethane film and the maximum force was measured and degree of tackiness assessed. The results are listed in Table 3.

EXAMPLE 16

Example 1 was repeated except that the PVA solution was replaced by 15.16% of an aqueous solution of Amaze® modified starch at 5% of active.

EXAMPLE 17 TO 19

Example 1 was repeated except that the PVA solution was replaced by 15.07% of an aqueous solution of various grades of Eastman AQ water-soluble sulfopolyester. Examples 17 to 19 used respectively 48S, 38S and 55S each at 5% of active. The results of Examples 16 to 19 are listed in Table 3.

TABLE 3

| | Film-Former | Active % film former solution | Active PVA/Active surfactant (wt %) | Force Max (Kg) | Degree of Tackiness |
|---|---|---|---|---|---|
| Example 3 | PVA 30-88 | 10.0 | 0.90 | 0.092 | 3-4 |
| Example 9 | Polyox ® WSR308 | 1.00 | 0.10 | 0.077 | 4 to 5 |
| Example 10 | Polyox ® WSR205 | 5.00 | 0.50 | 0.106 | 4 to 5 |
| Example 11 | Polyox ® WSR-N10 | 5.00 | 0.50 | 0.064 | 4 to 5 |
| Example 12 | Polyox ® WSR- N750 | 5.00 | 0.50 | 0.099 | 4 |
| Example 13 | Polyox ® WSR-N12K | 5.00 | 0.50 | 0.086 | 4 |
| Example 14 | Polyox ® WSR301 | 5.00 | 0.50 | 0.094 | 4 |
| Example 15 | Polyox ® WSR-N10K | 5.00 | 0.50 | 0.085 | 4 |
| Example 16 | Amaze | 5.00 | 0.51 | 0.073 | 3 |
| Example 17 | Eastman AQ48S | 5.00 | 0.50 | 0.102 | 4 to 5 |
| Example 18 | Eastman 38S | 5.00 | 0.50 | 0.095 | 4 to 5 |
| Example 19 | Eastman 55S | 5.00 | 0.50 | 0.080 | 4 to 5 |

All of Examples 3 and 9 to 17 coated on polyurethane film form a tacky adhesive layer as can be seen from the values of the Force max and confirmed by finger touch assessment.

The invention claimed is:
1. An aqueous dispersion capable of forming a tacky layer on drying, the aqueous dispersion comprising:
  A) a silicone composition dispersed in an aqueous phase, the silicone composition comprising a product of a reaction of;
    (a) an alkenyl-containing organopolysiloxane having an average per molecule of at least 2 alkenyl groups, wherein the alkenyl-containing organopolysiloxane
(a) is a branched siloxane comprising:
i) one or more units of the formula $SiO_{4/2}$;
ii) from 15 units to 995 units of the formula $Rb_2SiO_{2/2}$ where units i) and ii) may be interlinked in any appropriate combination; and
iii) units of the formula $RaRb_2SiO_{1/2}$ where each Ra substituent is selected from the group consisting of an alkyl group having from 1 to 6 carbon atoms and an alkenyl group having up to 6 carbon atoms and where each Rb substituent is selected from the group consisting of an alkyl group having from 1 to 6 carbon atoms, an alkenyl group having 2 to 6 carbon atoms, an aryl group, an alkoxy group, an acrylate group and a methacrylate group, and
(b) an SiH containing siloxane having an average per molecule of at least 2 SiH moieties;
B) a hydrosilylation catalyst;
C) a polymeric film former; and
D) a surfactant of molecular weight below 1600;
wherein the silicone composition A) is stabilised in dispersion form by the polymeric film former C) and the surfactant D) dissolved in the aqueous phase.

2. The aqueous dispersion according to claim 1, wherein the alkenyl-containing organopolysiloxane (a) has a dynamic viscosity of from 100 milliPascal-seconds (mPa·s) to 100,000,000 mPa·s when tested as described in ASTM D1084 at 25° C.

3. The aqueous dispersion according to claim 1, wherein the SiH containing siloxane (b) has an average per molecule of greater than 2 SiH moieties.

4. The aqueous dispersion according to claim 1, wherein the polymeric film former C) is a polyvinyl alcohol.

5. The aqueous dispersion according to claim 1, wherein the polymeric film former C) is a polyether, anionic polymer, polyester, polysaccharide, chitosan derivative, plasticized nitrocellulose, vinylpyrrolidone polymer, polyacrylate, polymethacrylate, polyacrylamide, polyacrylonitrile or polyurethane.

6. The aqueous dispersion according to claim 1, wherein the weight/weight ratio of the polymeric film former C) to the surfactant D) is in the range from 1:10 to 10:1.

7. The aqueous dispersion according to claim 1, wherein the polymeric film former C) is present at from 1 to 10% of the total weight of the aqueous dispersion.

8. The aqueous dispersion according to claim 1, wherein the pH of the aqueous phase of the aqueous dispersion is below pH 6.

9. A process for preparing the aqueous dispersion according to claim 1, the process comprising:
mixing the alkenyl-containing organopolysiloxane (a) and the SiH containing siloxane (b); and
emulsifying the resulting mixture in an aqueous solution of the polymeric film former C) and the surfactant D) to form an aqueous silicone emulsion;
wherein the hydrosilylation catalyst B) is added simultaneously with the aqueous solution of the polymeric film former C) and the surfactant D) or is added to the aqueous silicone emulsion subsequently;
wherein the alkenyl-containing organopolysiloxane (a) and the SiH containing siloxane (b) react together in the aqueous silicone emulsion; and
wherein the alkenyl-containing organopolysiloxane (a), the SiH containing siloxane (b) and their reaction product are stabilised in dispersion form by the polymeric film former C) and the surfactant D).

10. The process according to claim 9, wherein the mixing step comprises mixing an excipient oil with the alkenyl-containing organopolysiloxane (a) and the SiH containing siloxane (b) such that the resulting mixture further comprises the excipient oil before the emulsifying step.

11. A method of coating a substrate with a tacky layer comprising coating the substrate with the aqueous dispersion according to claim 1 and allowing a sufficient amount of water in the aqueous phase to evaporate from the coating on the substrate so as to form the tacky layer on the substrate.

12. A method of adhering a dressing to a mammal in need of such treatment with an aqueous dispersion comprising an aqueous phase, the method comprising either:
a) topically applying an effective amount of the aqueous dispersion to a portion of skin of the mammal, allowing a sufficient amount of water in the aqueous phase to evaporate from the aqueous dispersion so as to form a tacky layer on the portion of the skin, and applying the dressing to the said tacky layer on the portion of skin; or
b) coating a surface of the dressing with an effective amount of the aqueous dispersion, allowing a sufficient amount of water in the aqueous phase to evaporate from the coating so as to form a tacky layer on the surface of the dressing, and applying the tacky layer on the dressing to a portion of skin of the mammal;
wherein the aqueous dispersion comprises:
A) a silicone composition dispersed in the aqueous phase, the silicone composition comprising a product of a reaction of;
(a) an alkenyl-containing organopolysiloxane having an average per molecule of at least 2 alkenyl groups, and
(b) an SiH containing siloxane having an average per molecule of at least 2 SiH moieties;
B) a hydrosilylation catalyst;
C) a polymeric film former; and
D) a surfactant of molecular weight below 1600; and
wherein the silicone composition A) is stabilised in dispersion form by the polymeric film former C) and the surfactant D) dissolved in the aqueous phase.

13. A pharmaceutical or cosmetic composition comprising an admixture of the aqueous dispersion according to claim 1 and a pharmaceutically or cosmetically active ingredient, respectively.

14. A method of treating a disease or condition in a mammal in need of such treatment, the method comprising:
topically applying a therapeutically effective amount of a pharmaceutical or cosmetic composition to a portion of skin of the mammal;
wherein the pharmaceutical or cosmetic composition comprises an admixture of an aqueous dispersion and a pharmaceutically or cosmetically active ingredient, respectively, the aqueous dispersion comprising:
A) a silicone composition dispersed in an aqueous phase, the silicone composition comprising a product of a reaction of;
(a) an alkenyl-containing organopolysiloxane having an average per molecule of at least 2 alkenyl groups, and
(b) an SiH containing siloxane having an average per molecule of at least 2 SiH moieties;
B) a hydrosilylation catalyst;
C) a polymeric film former; and
D) a surfactant of molecular weight below 1600;

wherein the silicone composition A) is stabilised in dispersion form by the polymeric film former C) and the surfactant D) dissolved in the aqueous phase.

15. The aqueous dispersion according to claim 8, wherein the pH of the aqueous phase of the aqueous dispersion is below pH 5.

16. An adhesive for adhering a dressing to a patient, the adhesive comprising the aqueous dispersion according to claim 1.

17. A method of delivering a pharmaceutically or cosmetically active agent to a patient, the method comprising topically applying a pharmaceutical or cosmetic composition according to claim 13 to the patient.

18. The method according to claim 12, wherein the alkenyl-containing organopolysiloxane (a) is a branched siloxane comprising:
  i) one or more units of the formula $SiO_{4/2}$;
  ii) from 15 units to 995 units of the formula $Rb_2SiO_{2/2}$ where units i) and ii) may be inter-linked in any appropriate combination; and
  iii) units of the formula $RaRb_2SiO_{1/2}$ where each Ra substituent is selected from the group consisting of an alkyl group having from 1 to 6 carbon atoms and an alkenyl group having up to 6 carbon atoms and where each Rb substituent is selected from the group consisting of an alkyl group having from 1 to 6 carbon atoms, an alkenyl group having 2 to 6 carbon atoms, an aryl group, an alkoxy group, an acrylate group and a methacrylate group.

19. The method according to claim 14, wherein the alkenyl-containing organopolysiloxane (a) is a branched siloxane comprising:
  i) one or more units of the formula $SiO_{4/2}$;
  ii) from 15 units to 995 units of the formula $Rb_2SiO_{2/2}$ where units i) and ii) may be inter-linked in any appropriate combination; and
  iii) units of the formula $RaRb_2SiO_{1/2}$ where each Ra substituent is selected from the group consisting of an alkyl group having from 1 to 6 carbon atoms and an alkenyl group having up to 6 carbon atoms and where each Rb substituent is selected from the group consisting of an alkyl group having from 1 to 6 carbon atoms, an alkenyl group having 2 to 6 carbon atoms, an aryl group, an alkoxy group, an acrylate group and a methacrylate group.

* * * * *